United States Patent
Hardee et al.

(10) Patent No.: US 10,332,418 B2
(45) Date of Patent: Jun. 25, 2019

(54) PERSONALIZED VITAMIN SUPPLEMENT

(71) Applicant: International Business Machines Corporation, Armonk, NY (US)

(72) Inventors: Christopher James Hardee, Raleigh, NC (US); Steve Joroff, Tokyo (JP); Pamela Ann Nesbitt, Ridgefield, CT (US); Scott Edward Schneider, Rolesville, NC (US)

(73) Assignee: International Business Machines Corporation, Armonk, NY (US)

( * ) Notice: Subject to any disclaimer, the term of this patent is extended or adjusted under 35 U.S.C. 154(b) by 302 days.

(21) Appl. No.: 14/948,811

(22) Filed: Nov. 23, 2015

(65) Prior Publication Data

US 2017/0148348 A1  May 25, 2017

(51) Int. Cl.
| | |
|---|---|
| *G09B 19/00* | (2006.01) |
| *G01N 33/20* | (2019.01) |
| *G01N 33/00* | (2006.01) |
| *C12Q 1/02* | (2006.01) |
| *A61B 5/00* | (2006.01) |

(52) U.S. Cl.
CPC ........... *G09B 19/0092* (2013.01); *C12Q 1/02* (2013.01); *G01N 33/0047* (2013.01); *G01N 33/20* (2013.01); *A61B 5/486* (2013.01); *A61B 5/4866* (2013.01); *A61B 2560/0242* (2013.01)

(58) Field of Classification Search
None
See application file for complete search history.

(56) References Cited

U.S. PATENT DOCUMENTS

| | | |
|---|---|---|
| 5,954,640 A | 9/1999 | Szabo |
| 6,510,430 B1 | 1/2003 | Oberwager et al. |
| 7,136,820 B1 | 11/2006 | Petrus |
| 7,953,613 B2 | 5/2011 | Gizewski |

(Continued)

FOREIGN PATENT DOCUMENTS

EP    2392509 A1    7/2011

OTHER PUBLICATIONS

Egner; 2014; "Rapid and Sustainable Detoxication of Airborne Pollutants by Broccoli Sprout Beverage: Results of a Randomized Clinical Trial in China"; https://www.ncbi.nlm.nih.gov/pubmed/24913818.*

(Continued)

*Primary Examiner* — Eddy Saint-Vil
*Assistant Examiner* — William D Ermlick
(74) *Attorney, Agent, or Firm* — Cahn & Samuels, LLP

(57) ABSTRACT

An embodiment of the invention provides a method of collecting data to provide a personalized nutrition recommendation to a user, including receiving input from a sensor and/or an interface of a wearable electronic device of the user. The input includes physiological factors and/or environmental factors measured by the wearable electronic device, the environmental factors including sun exposure and air quality. A processor connected to the sensor and/or interface predicts nutritional deficiencies based on the input. The processor generates a personalized supplement recommendation for the user based on the nutritional deficiencies. The personalized supplement recommendation is displayed to the user on a display connected to the processor.

12 Claims, 3 Drawing Sheets

(56) References Cited

U.S. PATENT DOCUMENTS

| | | | | |
|---|---|---|---|---|
| 8,398,546 | B2* | 3/2013 | Pacione | A61B 5/411 128/920 |
| 8,428,622 | B1* | 4/2013 | Zhang | H04W 4/023 455/456.3 |
| 8,475,367 | B1* | 7/2013 | Yuen | G06F 19/3418 128/920 |
| 8,478,612 | B2 | 7/2013 | Kashani et al. | |
| 8,708,904 | B2 | 4/2014 | Stivoric et al. | |
| 9,883,340 | B2* | 1/2018 | Boldyrev | H04W 4/023 |
| 2005/0113650 | A1* | 5/2005 | Pacione | A61B 5/411 600/300 |
| 2009/0192365 | A1* | 7/2009 | Gisel | G06F 19/3475 600/301 |
| 2009/0275002 | A1* | 11/2009 | Hoggle | G09B 19/0092 434/127 |
| 2010/0217099 | A1* | 8/2010 | LeBoeuf | A61B 5/00 600/301 |
| 2011/0014351 | A1* | 1/2011 | Reider | G06F 19/3475 426/648 |
| 2011/0054928 | A1 | 3/2011 | Sullivan | |
| 2011/0191272 | A1* | 8/2011 | McGuire | G06N 5/00 706/11 |
| 2012/0083669 | A1* | 4/2012 | Abujbara | G06F 19/3475 600/300 |
| 2012/0233002 | A1* | 9/2012 | Abujbara | G06Q 10/06 705/15 |
| 2013/0216982 | A1* | 8/2013 | Bennett | G09B 5/00 434/127 |
| 2013/0267794 | A1* | 10/2013 | Fernstrom | G01N 33/02 600/301 |
| 2013/0297698 | A1* | 11/2013 | Odero | H04L 69/24 709/204 |
| 2014/0046591 | A1* | 2/2014 | Boldyrev | G01C 21/3438 701/533 |
| 2014/0052567 | A1* | 2/2014 | Bhardwaj | G06Q 30/0631 705/26.7 |
| 2014/0088996 | A1 | 3/2014 | Damani | |
| 2014/0107932 | A1* | 4/2014 | Luna | G01D 21/00 702/19 |
| 2014/0129243 | A1 | 5/2014 | Utter, II | |
| 2014/0236759 | A1* | 8/2014 | Mirabile | G06Q 30/0633 705/26.8 |
| 2014/0309806 | A1* | 10/2014 | Ricci | B60Q 1/00 701/1 |
| 2015/0093725 | A1* | 4/2015 | Baarman | G06F 19/3475 434/127 |
| 2015/0102208 | A1* | 4/2015 | Appelboom | G06F 19/3481 250/208.2 |
| 2015/0125832 | A1* | 5/2015 | Tran | G09B 19/0092 434/127 |
| 2015/0172855 | A1* | 6/2015 | Mishra | H04W 4/02 455/418 |
| 2015/0262507 | A1* | 9/2015 | Hanlon | G06F 19/3475 434/127 |
| 2016/0012748 | A1* | 1/2016 | Donavon | G09B 5/02 434/225 |
| 2016/0125747 | A1* | 5/2016 | Chou | G09B 5/00 434/236 |
| 2016/0232625 | A1* | 8/2016 | Akutagawa | G06Q 50/12 |
| 2016/0239624 | A1* | 8/2016 | Short | G06F 19/18 |
| 2017/0031449 | A1* | 2/2017 | Karsten | G06F 19/3418 |
| 2017/0156386 | A1* | 6/2017 | Baetge | A23L 33/10 |
| 2017/0193369 | A1* | 7/2017 | Ferrell | G06N 5/022 |
| 2017/0249445 | A1* | 8/2017 | Devries | G06F 19/3475 |

OTHER PUBLICATIONS

Gonzalez, Zurine D., "The New Smart Wristbands for 2015", [retrieved on Nov. 3, 2015]. Retrieved from the Internet <URL: https://www.wearable-technologies.com/2015/02/the-news-smart-wristbands-for-2015/>.

Handwerk, Brian, "With Wearable Devices That Monitor Air Quality, Scientists Can Crowdsource Pollution Maps", [retrieved on Nov. 13, 2015]. Retrieved from the Internet <URL: http://www.smithsonianmag.com/innovation/with-wearable-devices-that-monitor-air-quality-scientists-can-crowdsource-pollution-maps-180954556/#dKtUcQiDjj2BF6bm.99>.

Zareva, Teodora, "This Wearable Device Measures Your Personal Air Pollution and UV Exposure in Real-time", [retrieved on Nov. 13, 2015]. Retrieved from the Internet <URL: http://bigthink.com/design-for-good/this-wearable-device-measures-your-personal-air-pollution-and-uv-exposure-in-real-time>.

Rodin, Madeline, "A Wearable Pollution Monitor", [retrieved on Nov. 13, 2015]. Retrieved from the Internet <URL: http://www.popsci.com/wearable-pollution-monitor>.

Morin, Kate, "83 Healthy Recipe Substitutions", [retrieved on Nov. 13, 2015]. Retrieved from the Internet <URL: http://greatist.com/health/83-healthy-recipe-substitutions>.

Dunkin, Mary Anne, "Super Foods for Optimal Health", [retrieved on Nov. 13, 2015]. Retrieved from the Internet <URL: http://www.webmd.com/food-recipes/antioxidants-your-immune-system-super-foods-optimal-health>.

Air.Air! Portable Air Quality detector, https://www.kickstarter.com/projects/1886143677/airair-portable-air-quality-detector, printed on Feb. 19, 2018.

Craft, Microsensors help map crowdsourced pollution data, Jun. 2013, http://www.greenbiz.com/blog/2013/06/26/microsensing-measure-air-pollution-palm-your-hand.

Vitamin C Might Protect Lungs on High PollutionDays: Study, Aug. 2012, http://www.huffingtonpost.com/2012/08/19/vitamin-c-pollution-lungs-antioxidants-particulate-matter_n_1797797.html.

Vitamin D Council: How do I get the vitamin D my body needs?, http://www.vitamindcouncil.org/about-vitamin-d/how-do-i-get-the-vitamin-d-my-body-needs/, printed on Feb. 19, 2018.

Kotz, Time in the Sun: How Much is Needed for Vitamin D?, Jun. 2008, http://health.usnews.com/health-news/family-health/heart/articles/2008/06/23/time-in-the-sun-how-much-is-needed-for-vitamin-d.

Calculated Ultraviolet Exposure Levels or a Healthy Vitamin D Status, http://nadir.nilu.no/~olaeng/fastrt/VitD-ez_quartMED.html, printed on Feb. 19, 2018.

\* cited by examiner

PERSONALIZED VITAMIN SUPPLEMENT

BACKGROUND

The present invention relates to systems, methods, and computer program products for personalized vitamin supplements. Dietitians and other nutritional experts can create customized meal plans to meet their client's nutritional needs. Such meal plans can be created based on information provided by the clients, such as current fitness goals, food profiles, health histories, familial histories, and current health status. For instance, if a client is on a diet, he or she might need supplements to counterbalance the lack of certain food elements necessary to health. Furthermore, vegetarians may not be getting enough iron; and, a familial history of Alzheimer's disease might indicate the need for vitamin E, which may promote brain health. Pregnant women may need different vitamins and that can vary by pregnancy stage.

SUMMARY OF THE INVENTION

An embodiment of the invention provides a method of collecting data to provide a personalized nutrition recommendation to a user, including receiving input from a sensor and/or an interface of a wearable electronic device of the user. The input includes physiological factors and/or environmental factors measured by the wearable electronic device, the environmental factors including sun exposure and air quality. A processor connected to the sensor and/or interface predicts nutritional deficiencies based on the input. The processor generates a personalized supplement recommendation for the user based on the nutritional deficiencies. The personalized supplement recommendation is displayed to the user on a display connected to the processor.

BRIEF DESCRIPTION OF THE SEVERAL VIEWS OF THE DRAWINGS

The present invention is described with reference to the accompanying drawings. In the drawings, like reference numbers indicate identical or functionally similar elements.

DETAILED DESCRIPTION

Figure 1:
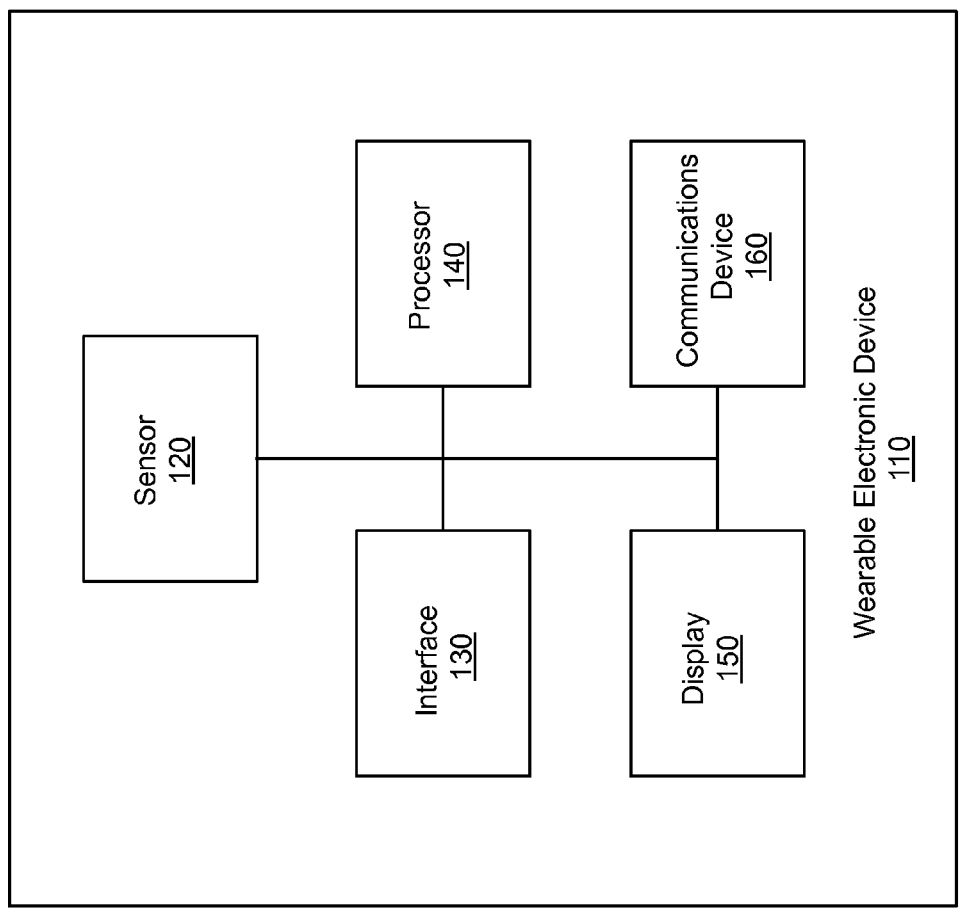
FIG. 1 is a diagram illustrating a system for generating a personalized vitamin supplement according to an embodiment of the invention.

Exemplary, non-limiting, embodiments of the present invention are discussed in detail below. While specific configurations are discussed to provide a clear understanding, it should be understood that the disclosed configurations are provided for illustration purposes only. A person of ordinary skill in the art will recognize that other configurations may be used without departing from the spirit and scope of the invention.

At least one embodiment of the invention provides a system that generates a custom vitamin supplement recommendation using input from wearable electronic devices. The input can include, for example, sun exposure, food intake, exercise, perspiration, etc. The custom vitamin supplement recommendation can also be generated based on historical details about the user along with current concerns and goals.

The system can determine a nutritional baseline for the user using elements such as demographic information, health history, nutrient profiles, familial history (e.g., family history of Alzheimer's disease may indicate the need for vitamin E, which is said to promote brain health), current status (e.g., pregnant women may need different vitamins, which may vary by pregnancy stage), and/or information entered by the user. The information entered by the user can include current goal(s) and/or a food profile. For example, if a current goal of the user is to diet, the user may need supplements to counterbalance a lack of certain food elements necessary to health. In another example, if the user's food profile indicates that he is a vegetarian, he may not be getting enough iron in his diet.

In at least one embodiment of the invention, the system includes a wearable electronic device, or receives data from a wearable electronic device, that measures exercise activity, planned exercise, food intake, sun exposure, air quality, sleep, sweat, and/or human waste. Such data can be measured directly by the wearable electronic device and/or manually entered into the system or the wearable electronic device (e.g., by the user). For instance, the user can enter food intake into the wearable electronic device. The user can enter what was consumed, when it was consumed, and the calories of what was consumed. In one embodiment, calories can be calculated by the wearable electronic device based on the user's input. In another embodiment, caloric consumption can be tracked by via image acquisition by the wearable electronic device. Specifically, the user can take a photograph of his or her food prior to consumption, and the wearable electronic device can estimate caloric consumption based on the photograph. In yet another embodiment, data (e.g., planned exercise, food intake) can be input into the wearable electronic device from one or more wirelessly connected devices (e.g., via Bluetooth), such as a smartphone, a laptop, or a tablet computer.

Data that can be input into or monitored by the wearable electronic device (e.g., via its sensors) can also be received as input by the wearable electronic device from external electronic devices (e.g., the user's smartphone). For instance, the user's exercise activity can be manually entered, calculated and/or monitored by the wearable electronic device, or the user's exercise activity can be wirelessly received as input from the user's smartphone. Exercise activity can include the type and quantity of exercise (e.g., run 5 miles, 50 sit ups, 100 jumping jacks, 20 pushups, etc.). The wearable electronic device can measure the user's movements, duration of the movements, intensity of the movements, and/or heart rate. Moreover, the wearable electronic device can calculate calories burned based on the measurements and stored user parameters, such as, for example, weight, height, age, body fat percentage, gender, etc. Furthermore, the user's planned exercise can be manually entered into the wearable electronic device. Therefore, the user's scheduled events or workouts can be used to preemptively estimate the supplement needs.

The user's sun exposure can be measured or entered into the wearable electronic device. The body can synthesize vitamin D (specifically cholecalciferol) in the skin, from cholesterol, when sun exposure is adequate (hence its nickname, the "sunshine vitamin"). Air quality, which can increase the need for anti-oxidants such as Vitamin E, can be measured, entered, or downloaded into the wearable electronic device (e.g., based on the user's location). People can be exposed to free radicals in the environment from cigarette smoke, air pollution, and ultraviolet light from the sun. Details of the user's waste, such as type (excrement, urine) and when and how much was discharged can be entered into the wearable electronic device. Details of the user's sweat can be entered or measured by the wearable electronic device. Dehydration from excessive sweating can deplete water-soluble vitamins from the body.

Details of the user's sleep, such as time of sleep and time of awake can be entered into the wearable electronic device. Numerous factors can contribute to poor sleep, including vitamin and mineral deficiencies. Melatonin is both a hormone and an antioxidant; a magnesium deficiency can cause insomnia; lack of potassium can lead to difficulty staying asleep throughout the night; and, a vitamin D deficiency has been linked to excessive daytime sleepiness. In at least one embodiment, one or more motion sensors (e.g., actigraph, accelerometer) in the wearable electronic device identifies tossing and turning during the night, which can indicate poor sleep. The wearable electronic device can also identify the behavior of the user after a poor night's sleep (e.g., sluggishness, metabolic differences, drinking more coffee, eating more sweets). For instance, the wearable electronic device can include three sensors for measuring the heart, movement and metabolic rates of a user. The wearable electronic device can give constant updates and syncs through online devices, for example via Bluetooth. Furthermore, the wearable electronic device can track and monitor exercise programs to inform a user whether he or she is meeting daily and weekly goals for fitness, health and well-being. This can be used to benchmark performance and compare specific days or activities against those benchmarks.

The system (which can include or be separate from the wearable electronic device) can tailor a supplement recommendation using the data measured and/or entered into the wearable electronic device. In an embodiment where the system is separate from the wearable electronic device, such data can be manually entered into an interface of the system instead of into the wearable electronic device. The supplement recommendation can be designed to be taken by the user at specified intervals (e.g., daily, twice a day, after meals). The time of day in which the supplement recommendation is to be consumed can be tailored to its effect on sleepiness/wakefulness, nausea (a common side effect of multivitamins and others when taken on empty stomach), and their interaction with medications taken during the day.

In addition, the system can suggest food or drinks to replace some of the nutrients that would be included in the supplement, such as a glass of orange juice, which would reduce the need for vitamin C in the supplement. The system can use the inventory of the user's kitchen to determine what was available for suggestions. If the user responds or fails to respond to the personalized supplement in a measurable and unexpected way, a suggestion to see a doctor can be made. In at least one embodiment, data from the system is shared with a physician.

Figure 2:
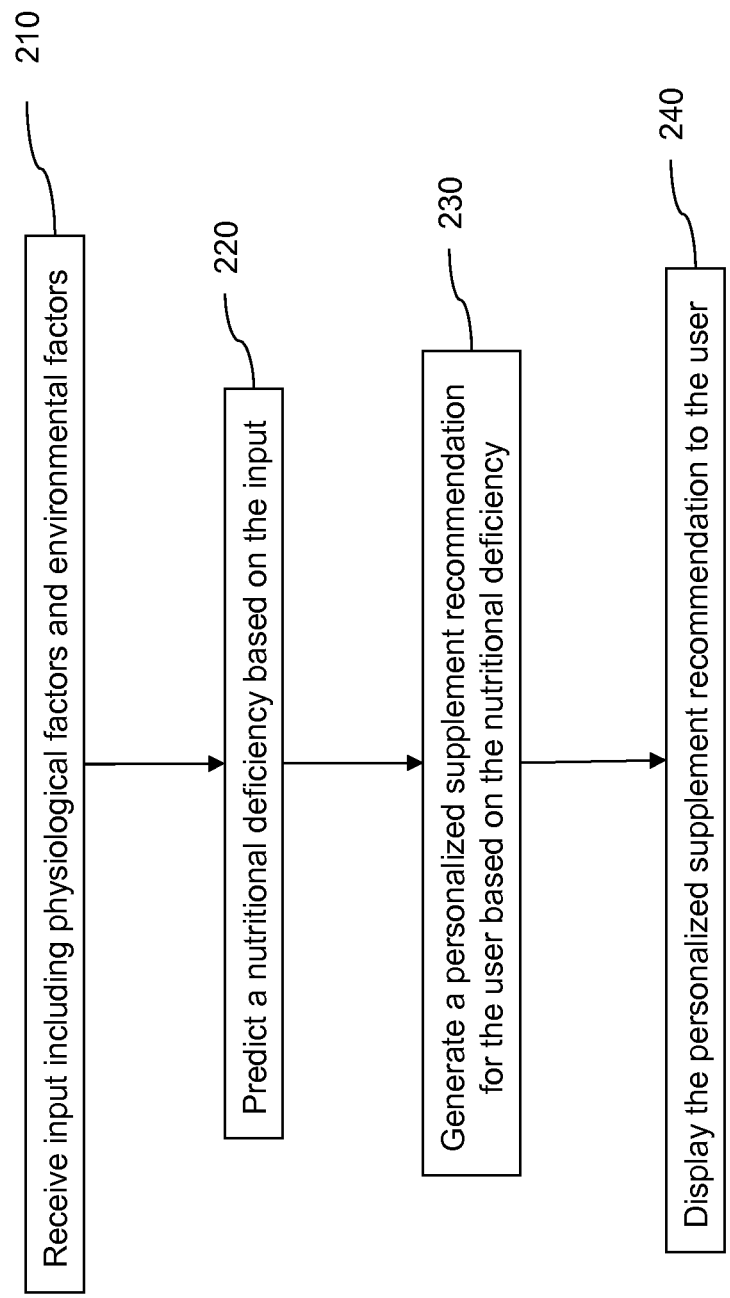
FIG. 2 is a flow diagram illustrating a method for generating a personalized vitamin supplement according to an embodiment of the invention.

FIG. 1 is a diagram illustrating a device for generating a personalized vitamin supplement according to an embodiment of the invention. FIG. 2 is a flow diagram illustrating a method for generating a personalized vitamin supplement according to an embodiment of the invention (e.g., using the device illustrated in FIG. 1). The device can be a wearable electronic device 110, such as for example, a wrist band, wrist watch, chest strap, necklace, pendant, headwear (e.g., hair pin, hair band, hat, visor), or a smartphone. The wearable electronic device 110 can include a sensor 120 (e.g., heart beat monitor, motion detector, light sensor) and/or an interface 130 (e.g., touchscreen, keypad, usb port). In at least one embodiment, the wearable electronic device 110 includes a plurality of devices configured to monitor one or more health characteristics.

The sensor 120 and/or the interface 130 can receive input including physiological factors and/or environmental factors (e.g., measured and/or received by the wearable electronic device 110) (210). The environmental factors can include sun exposure and/or air quality. For instance, the sensor 120 can measure the amount of time that the wearable electronic device 110 is exposed to a light threshold level (e.g., greater than 500 lumens) in a given time period (e.g., 24 hours). As described below, the personalized supplement recommendation can be based on this measurement.

The sensor 120 can also measure the amount of airborne toxins (e.g., lead, benzene, mercury, mold) and/or the amount of particulate matter (e.g., measured in milligrams) that the wearable electronic device is exposed to in a given time period (e.g., 4 days). In another embodiment, the sun exposure and/or air quality data is entered into the wearable electronic device 110 via the interface 130 and/or an antenna in the wearable electronic device 110, the antenna receiving the sun exposure and/or air quality data from an environmental monitor (e.g., location specific) broadcasting information wirelessly.

The physiological factors can relate to the biological functions and activities of the user and can include blood pressure, hydration level, sweat salt content, sweat volume/amount, caloric consumption, caloric expenditure (e.g., based on measured motion/movement), planned exercise (e.g., based on user's calendar), human waste amount, human waste type, amount of sleep, sleep quality (e.g., user rating system (e.g., scale of 1-10, star rating), movement/tossing and turning measured by a motion sensor), the time that the user went to sleep, the time that the user woke up, amount of sleep, and amount of being awake.

A processor 140 connected to the wearable electronic device 110 can predict one or more nutritional deficiencies of the wearer of the wearable electronic device 110 (also referred to herein as the "user"). As used herein, the term "connected" includes operationally connected, logically connected, in communication with, physically or wirelessly connected, engaged, coupled, contacts, linked, affixed, attached, integral, internal, and/or positioned on. For instance, although FIG. 1 illustrates that the processor 140 is an integral part of the wearable electronic device 110, it is recognized in another embodiment that the processor 140 can be external to the wearable electronic device 110. The processor 140 can predict the nutritional deficiency (e.g., melatonin) based on the input (e.g., sleep rating) (220).

The processor 140 can generate a personalized supplement recommendation for the user based on the nutritional deficiency (230). In at least one embodiment, the generating of the personalized supplement recommendation includes generating a recipe (e.g., list of ingredients and quantities) for producing the supplement. The personalized supplement recommendation can be displayed to the user on a display 150 connected to the processor 140 (240). Although FIG. 1 illustrates that the display 150 is an integral part of the wearable electronic device 110, it is recognized in another embodiment that the display 150 can be external to the wearable electronic device 110. In at least one embodiment, the processor 140 can send the personalized supplement recommendation to a 3D food printer (e.g., via a wireless communication device 160 on the processor 140).

The processor 140 can also generate a personalized supplement recommendation for an additional user that is positioned less than a threshold distance from the wearable electronic device 110 (e.g., 1 meter) when the wearable electronic device 110 received the input. The personalized supplement recommendation for the additional user can be generated based on the one or more nutritional deficiencies. For example, when the processor 140 determines that the user's exposure to sunlight is above a threshold, the processor 140 recommends a supplement including Vitamin E to the additional user. Poor air quality can increase the need for anti-oxidants such as Vitamin E. People can be exposed to free radicals in the environment from cigarette smoke, air pollution, and ultraviolet light from the sun. In at least one embodiment, the location of the additional user with respect to the wearable electronic device 110 is determined via GPS devices in the wearable electronic device 110 and an electronic device on the additional user (e.g., cellular telephone).

The processor 140 can also generate a meal recipe for the user, the meal recipe can include a list of ingredients and instructions for preparing the meal. The meal recipe can be generated based on the nutritional deficiency. The meal recipe can substitute new ingredients (with added health benefits, such as antioxidants) for something the user already has on his or her menu, or suggest different recipes. The processor 140 can also generate a dietary plan for the user, the dietary plan can include a list of meal recipes for at least one week. The dietary plan can be generated based on the nutritional deficiency. Additionally, the processor 140 can also generate a food additive for the user, the food additive can include a list of ingredients and instructions for preparing an additive to be added to food. The food additive (e.g., Vitamin A) can be generated based on the nutritional deficiency. Additives can include ingredients with known benefits for the use. In addition, simple supplements can be added granularly. For instance, a Vitamin A supplement can be mixed into the recipe without significantly altering the taste.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 3:
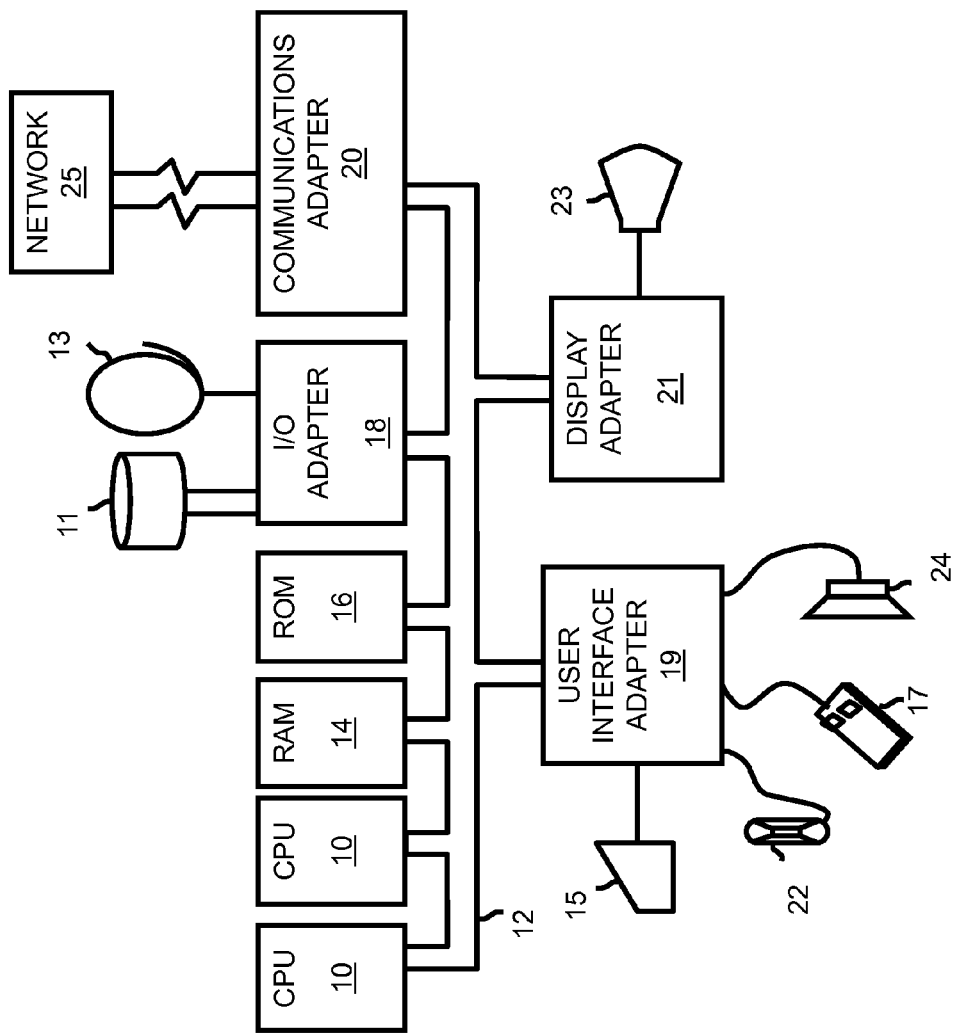
FIG. 3 is a diagram illustrating a computer program product according to an embodiment of the invention.

Referring now to FIG. 3, a representative hardware environment for practicing at least one embodiment of the invention is depicted. This schematic drawing illustrates a hardware configuration of an information handling/computer system in accordance with at least one embodiment of the invention. The system comprises at least one processor or central processing unit (CPU) 10. The CPUs 10 are interconnected with system bus 12 to various devices such as a random access memory (RAM) 14, read-only memory (ROM) 16, and an input/output (I/O) adapter 18. The I/O adapter 18 can connect to peripheral devices, such as disk units 11 and tape drives 13, or other program storage devices that are readable by the system. The system can read the inventive instructions on the program storage devices and follow these instructions to execute the methodology of at least one embodiment of the invention. The system further includes a user interface adapter 19 that connects a keyboard 15, mouse 17, speaker 24, microphone 22, and/or other user interface devices such as a touch screen device (not shown) to the bus 12 to gather user input. Additionally, a communication adapter 20 connects the bus 12 to a data processing network 25, and a display adapter 21 connects the bus 12 to a display device 23 which may be embodied as an output device such as a monitor, printer, or transmitter, for example.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the root terms "include" and/or "have", when used in this specification, specify the presence of stated features, integers, steps, operations, elements, and/or components, but do not preclude the presence or addition of at least one other feature, integer, step, operation, element, component, and/or groups thereof.

The corresponding structures, materials, acts, and equivalents of all means plus function elements in the claims below are intended to include any structure, or material, for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method, comprising:
   receiving input from a wearable electronic device of a user, the wearable device having a light sensor, accelerometer, an antenna, and a display, the input including
      physiological factors selected from the group consisting of an amount of sleep and sleep quality measured via the accelerometer, a time that the user went to sleep, a time that the user woke up, and an amount of being awake,
      additional user location information from a device of an additional user, and
      environmental factors including sun exposure via the light sensor and air quality via the antenna;
   generating, via a processor, a personalized supplement recommendation for the user based on nutritional deficiencies determined from the received input and the environmental factors, wherein the personalized supplement recommendation includes at least one of vitamin E when the light sensors detects sun exposure above a predetermined threshold, melatonin when the physiological factors indicate poor sleep and vitamin E when the antenna detects poor air quality;
   displaying the personalized supplement recommendation on the display of the wearable electronic device;
   sending the personalized supplement recommendation to a 3D printer and printing the personalized supplement at the 3D printer based on the recommendation;
   determining whether the additional user is within a threshold distance from the wearable electronic device; and
   generating an additional personalized supplement recommendation for the additional user based on the personalized supplement recommendation for environmental factors for the user when the additional user is within a threshold distance from the wearable electronic device.

2. The method according to claim 1, further comprising measuring an amount of time that the wearable electronic device is exposed sunlight above a predetermined threshold level.

3. The method according to claim 1, wherein the airborne toxin comprises lead, benzene, or mercury.

4. The method according to claim 1, wherein the generated personalized supplement recommendation is further based on a nutritional baseline including a familial history.

5. The method according to claim 4, wherein the nutritional baseline is based on a food profile entered by the user, wherein the food profile indicates the user is a vegetarian.

6. The method according to claim 1, wherein the wearable electronic device further comprises a heart beat monitor and a motion detector.

7. The method according to claim 1, wherein the antenna receives data from a location-specific environmental monitor that broadcasts information wirelessly.

8. The method according to claim 1, wherein the environmental factors further comprise cigarette smoke.

9. The method according to claim 1, wherein the personalized supplement recommendation is based on a melatonin deficiency.

10. The method according to claim 1, wherein the personalized supplement recommendation includes vitamin E.

11. The method according to claim 1, wherein the personalized supplement recommendation includes magnesium and potassium.

12. A non-transitory computer-readable medium having computer-readable instructions stored thereon which when executed by a computer cause the computer to perform a method, comprising:

receiving input from a wearable electronic device of a user, the wearable device having a light sensor, accelerometer, an antenna, and a display, the input including:
physiological factors selected from the group consisting of an amount of sleep, sleep quality measured via the accelerometer, a time that the user went to sleep, a time that the user woke up, and an amount of being awake, and
additional user location information from a device of an additional user,
environmental factors including sun exposure via the light sensor and air quality via the antenna;

generating a personalized supplement recommendation for the user based on nutritional deficiencies determined from the received input and the environmental factors, wherein the personalized supplement recommendation includes at least one of vitamin E when the light sensors detects sun exposure above a predetermined threshold, melatonin when the physiological factors indicate poor sleep and vitamin E when the antenna detects poor air quality;

displaying the personalized supplement recommendation on the display of the wearable electronic device;

sending the personalized supplement recommendation to a 3D printer and printing the personalized supplement at the 3D printer based on the recommendation;

determining whether the additional user is within a threshold distance from the wearable electronic device; and generating an additional personalized supplement recommendation for the additional user based on the personalized supplement recommendation for environmental factors for the user when the additional user is within a threshold distance from the wearable electronic device.

* * * * *